United States Patent [19]
Ricci

[11] Patent Number: 5,165,395
[45] Date of Patent: Nov. 24, 1992

[54] ULTRA-VIOLET GERMICIDAL MASK SYSTEM

[76] Inventor: Mark R. Ricci, 40 Hersey St., Hingham, Mass. 02043

[21] Appl. No.: 835,528

[22] Filed: Feb. 14, 1992

[51] Int. Cl.$^5$ .................. A61L 9/20; A61M 16/06
[52] U.S. Cl. .................. 128/202.22; 128/205.27; 128/206.12; 55/DIG. 35; 55/279
[58] Field of Search .................. 128/201.25, 202.22, 128/205.27, 205.29, 206.12, 206.13, 206.14, 206.15, 206.17, 202.25; 422/24, 2, 186.3; 55/267, 279, DIG. 9, DIG. 35

[56] References Cited

U.S. PATENT DOCUMENTS

| | | | |
|---|---|---|---|
| D. 250,047 | 10/1978 | Lewis et al. | |
| 3,672,129 | 6/1972 | Strople | 55/270 |
| 4,494,538 | 1/1985 | Ansite | 128/205.25 |
| 4,677,976 | 7/1987 | Fujinuma | 128/201.25 |
| 4,694,179 | 9/1987 | Lew | 250/431 |
| 4,786,812 | 11/1988 | Humphreys | 250/455.1 |
| 4,806,768 | 2/1989 | Keutenedjian | |
| 4,948,980 | 8/1990 | Wedekamp | 250/504 R |
| 4,951,662 | 8/2890 | Townsend, Jr. | |
| 5,003,974 | 4/1991 | Mou | 128/201.25 |
| 5,012,805 | 5/1991 | Muckerheide | |
| 5,018,518 | 5/1991 | Hübner | 128/202.22 |
| 5,037,618 | 8/1991 | Hager | 422/186.3 |
| 5,047,072 | 9/1991 | Wertz | 55/1 |

FOREIGN PATENT DOCUMENTS

| | | | |
|---|---|---|---|
| 2618127 | 11/1977 | Fed. Rep. of Germany | 422/24 |
| 2732859 | 2/1979 | Fed. Rep. of Germany | 422/24 |
| 729022 | 7/1932 | France | 422/24 |
| 2103095 | 2/1983 | United Kingdom | 128/201.25 |

*Primary Examiner*—Clifford D. Crowder
*Assistant Examiner*—Eric P. Raciti
*Attorney, Agent, or Firm*—Richard C. Litman

[57] ABSTRACT

A germicidal mask system to be worn by a user kills germs, viruses, or other pathogens which are located in the air to be breathed by the user. Before entering the mask, the air is exposed to ultra-violet radiation killing the undesirable germs, viruses, and other pathogens for which the ultra-violet radiation is lethal. In this manner only germ free air is provided to a user. Such a mask system would be useful to those users who are easily susceptible to contagious diseases. The germicidal mask system could also expose exhaled air from the user to kill any germs, viruses, or other pathogens exhaled by the user. Such a system would be useful to those who are continuously exposed to contagious diseases, such as doctors, or other health professionals, so as not to pass any diseases on to patients. This system also finds use in biological laboratories in order to prevent media cultures from being contaminated.

15 Claims, 4 Drawing Sheets

ULTRA-VIOLET GERMICIDAL MASK SYSTEM

BACKGROUND OF THE INVENTION

1. Field of the Invention

The present invention relates to face masks designed to prevent the transmission of germs and other pathogens to and from the wearer of the mask. More specifically, the present invention relates to those face masks in which the air going into the mask was subjected to radiation prior to entering the mask in order to kill any germs or other pathogens the air might have contained.

2. Description of the Prior Art

Masks, and more specifically surgical masks, are used to prevent germs and other pathogens from passing therethrough, while allowing total freedom of movement for the user wearing the mask.

U.S. Pat. No. 4,951,662 issued Aug. 28, 1990 to Townsend, Jr. discloses a surgical mask in which circulating air is provided within the mask to reduce humidity. The circulating air is provided by an electric fan powered by a battery pack, all of which is portable.

U.S. Pat. No. 5,012,805 issued May 7, 1991 to Muckerheide discloses a surgical mask with a non-porous exterior.

U.S. Des. Pat. No. 250,047 issued Oct. 24, 1978 to Lewis et al. discloses a mask with an air tube attached.

Devices used to sterilize rooms can use ultra-violet radiation for killing germs, viruses, and other pathogens located in the room.

U.S. Pat. No. 4,786,812 issued Nov. 22, 1988 to Humphreys discloses a device using ultra-violet lamps to sterilize surfaces in a room.

U.S. Pat. No. 4,806,768 issued Feb. 21, 1989 to Keutenedjian discloses a device for killing germs, viruses, and other pathogens in the air of a room through the use of ultra-violet and infra-red radiation.

None of the prior art of record discloses the use ultra-violet radiation for killing germs and other pathogens entering into a mask or exiting from the mask when worn by a user.

SUMMARY OF THE INVENTION

Accordingly, it is an object of the present invention to provide a germicidal mask system for killing germs, viruses, and other pathogens through the use of radiation.

It is another object of the present invention to prevent any of the radiation used by the present invention from harming the user wearing the mask or anyone in close proximity to the user.

It is still another object of the present invention to allow total freedom of movement of the user of the germicidal mask system.

These and other advantages of the present invention further enhancing and advancing the technology in the art will become clear upon further review of the following specification, drawings, and claims.

DETAILED DESCRIPTION OF THE PRESENT INVENTION

Figure 1:
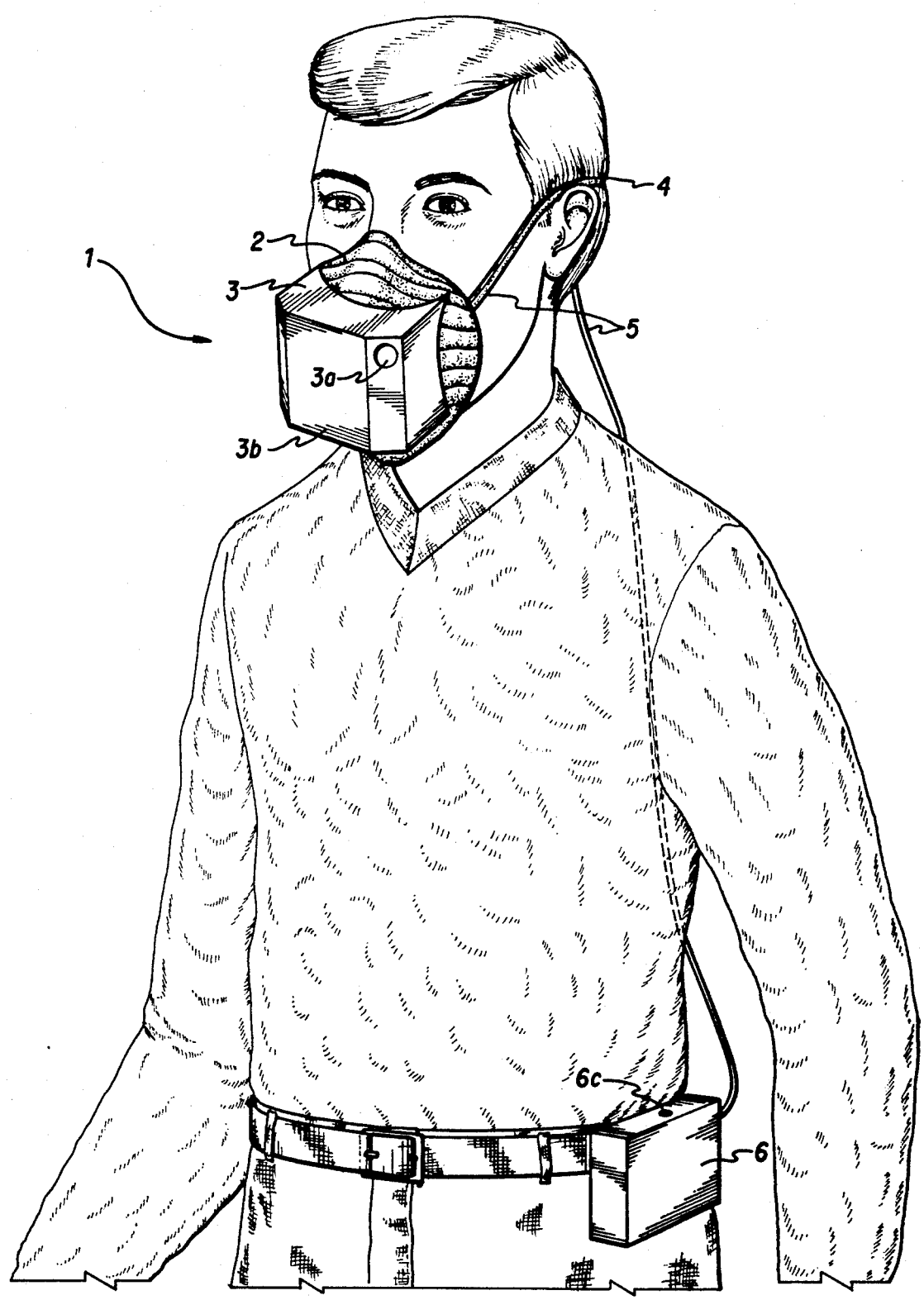
FIG. 1 is a perspective environmental view of the first embodiment of the present invention.

The germicidal mask system 1 of the first embodiment is illustrated in FIG. 1. As shown in FIG. 1, the user of the system wears a non-porous face mask 2 which is clear and flexible and provides an airtight fit over the nose and mouth. In front of the non-porous face mask 2 is a sterilization chamber 3 which is rigidly and securely attached thereto in any conventional manner, e.g., glued. An air passageway between the non-porous face mask 2 and the sterilization chamber 3 allows air to flow therebetween (see FIGS. 2 and 3). The sterilization chamber 3 is made of an opaque material or any other material impervious to ultra-violet radiation. Inside the sterilization chamber 3 is an ultra-violet light source which kills any undesirable microorganisms such as germs, viruses, or other pathogens to which the ultra-violet light is lethal (see FIG. 2 and 3). Another air passageway 3a is located on the outer cover 3b of the sterilization chamber 3 to allow air to flow between the ambient environment and the sterilization chamber 3. In this manner, air inhaled by the user first enters the sterilization chamber 3 and then the non-porous face mask 2, and any undesirable microorganisms which the air might have contained are killed inside the sterilization chamber 3 before the user breathes in the air. Likewise, as the user exhales into the non-porous face mask 2, the exhaled air enters the sterilization chamber 3 before exiting through the air passageway 3a to the ambient environment. In the same manner as the inhaled air was sterilized, the exhaled air is also exposed to the ultra-violet light to kill any undesirable micro-organisms within the air.

Figure 2:
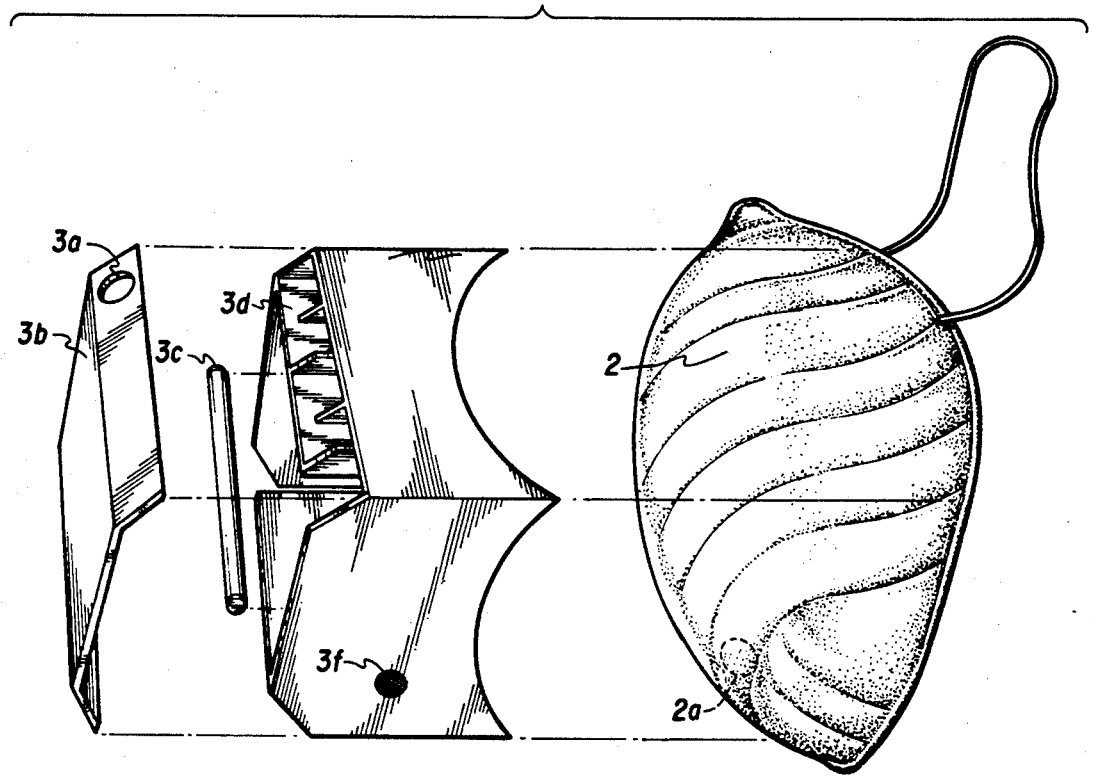
FIG. 2 is a perspective exploded view of the first embodiment of the present invention.
Figure 3:
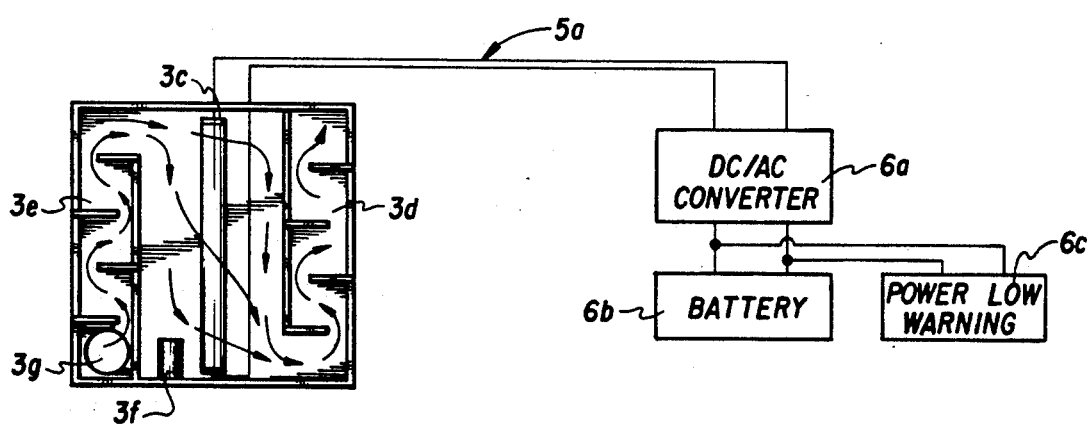
FIG. 3 is a front view of the first embodiment of the present invention with the cover removed.

As shown in FIG. 1, an elastic band 4 is used to hold the non-porous face mask 2 and the sterilization chamber 3 over the nose and mouth of the user in an airtight fashion. A battery pack 6 is used to provide the alternating current (a.c.) voltage necessary to operate the ultra-violet light source within the sterilization chamber 3. The battery pack can be fastened to an article of clothing worn by the user, such as the belt as shown in FIG. 1. An electrical wire 5 is used to supply the a.c. voltage from the battery pack 6 to the ultra-violet light source. The electrical wire 5 travels from the battery pack 6 in back of the user to the elastic band 4. The electrical wire 5 can travel along the outside of the elastic band 4 by being attached thereto as shown in FIG. 1 or it can travel inside the elastic band 4 to the sterilization chamber. As shown in FIG. 2, the ultra-violet light source discussed above is made up of a miniature ultraviolet lamp 3c. Between air passageway 3a and the miniature ultra-violet lamp 3c is a baffle arrangement 3d which prevents any ultra-violet radiation from exiting throug the air passageway 3a. As shown in FIG. 3, another baffle arrangement 3e prevents the ultraviolet radiation generated by the miniature ultraviolet lamp 3c from exiting through the air passageway going from the sterilization chamber 3 to the non-porous face mask 2. This air passageway is made up of a hole 3g in the back of the sterilization chamber 3 and a hole 2a in the front of the non-porous face mask 2, where the holes 3g and 2a overlap one another.

As shown in FIGS. 2 and 3, a disposable moisture absorbing cartridge 3f is connected to the bottom of the sterilization chamber 3 and may be selectively placed into or removed from the bottom. Further, as shown in FIG. 3, in order to generate the ultraviolet radiation, the miniature ultra-violet lamp 3c is connected to an a.c. power source supplied by a direct current to alternating current (dc/ac) converter 6a. The dc/ac converter 6a has its input connected to the battery 6b which supplies a d.c. voltage thereto. The battery 6b is preferably a rechargeable battery. With the d.c. voltage supplied to its input, the dc/ac converter 6a supplies an a.c. voltage to its output. Two conductors 5a which are insulated from one another, are part of the wire 5 as discussed above and carry the a.c. voltage from the output of the dc/ac converter 6a to the miniature ultra-violet lamp 3c. A power low warning circuit 6c monitors the voltage of the battery 6b and alerts the user when the battery 6b is low by the use of a light 6c as shown in FIG. 1 which lights up when the battery 6b is low. The light 6c comes on before the battery 6b is too low to operate the miniature ultra-violet lamp 3c. The dc/ac converter 6a, battery 6b, and the power low warning circuit 6c are all part of the batter pack 6 as illustrated in FIG. 1. While a light 6c is illustrated as the sole means to alert the user, an audio generator may be used instead or in conjunction therewith.

Figure 4:
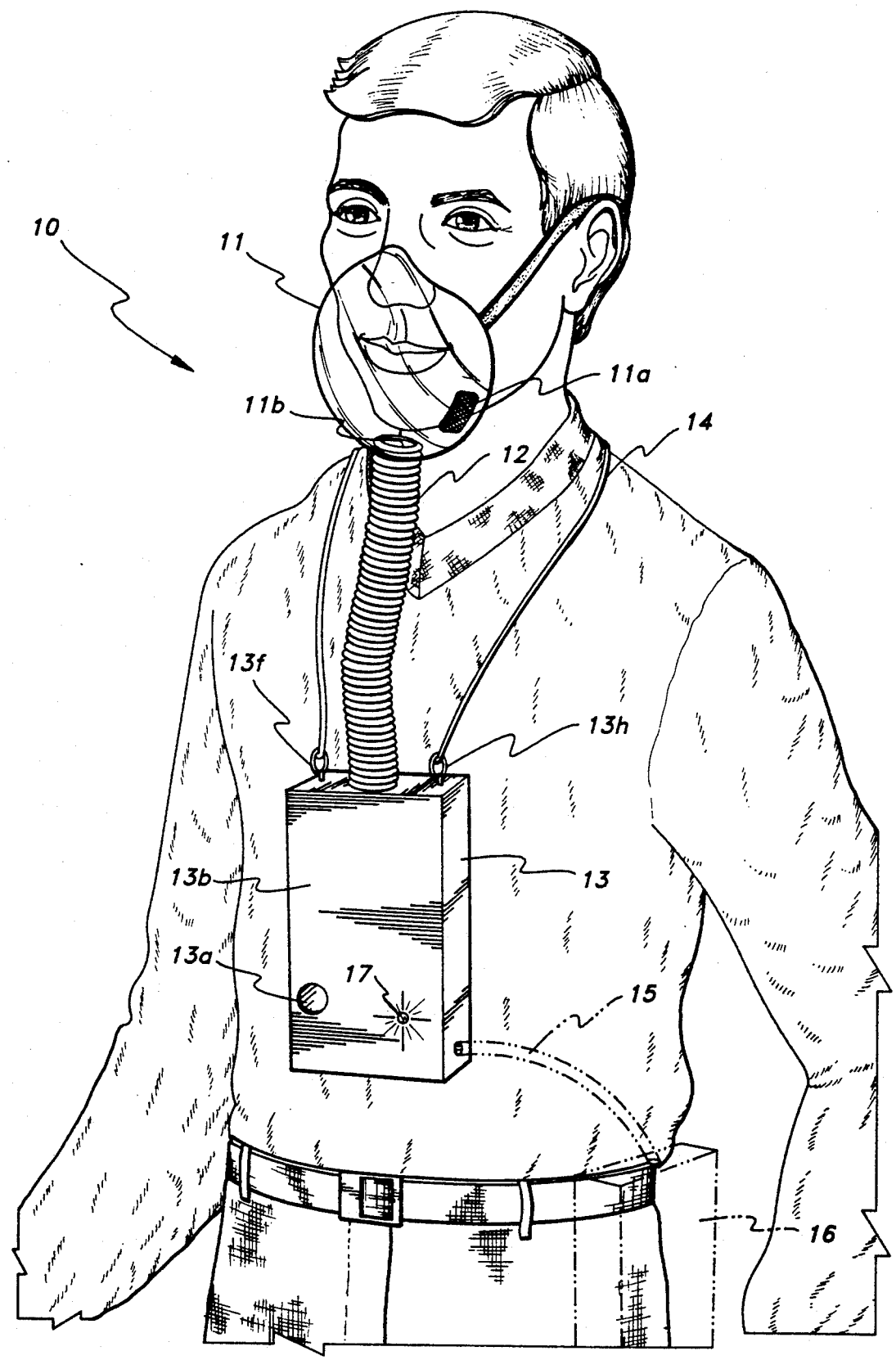
FIG. 4 is a perspective environmental view of the second embodiment of the present invention.

As shown in FIG. 4, a second embodiment of the present invention is illustrated. The first embodiment of the present invention was concerned with sterilizing the inhaled air of the user as well as the exhaled air of the user. Germicidal mask system 1 would be useful as a surgical mask since it would prevent germs and viruses from the patient from entering the doctor wearing the mask as well as prevent germs or viruses from the doctor from going to the patient. Germicidal mask system 1 would also be useful in biological laboratories where it could be used by the biological operators who handle and work with media cultures. System 1 would prevent germs or viruses grown in the cultures from entering the biological operators, while also preventing any germs or viruses from the biological operators from contaminating the media cultures. The second embodiment of the present invention as shown in FIG. 4, illustrates a germicidal mask system 10 having a non-porous face mask 11 which is clear and flexible and provides an airtight fit over the nose and mouth of the user wearing it. Unlike the germicidal mask system 1, the air within the non-porous face mask 11 enters from one location and exits through another. More specifically, as the user breathes in air which enters the sterilization chamber 13 through the air passageway 13a and travels up the air tube 12 which is flexible and clear, a one-way valve 11b opens to allow the sterilized air to enter the non-porous air mask 11. However, as the air is exhaled, the one-way valve 11b prevents the exhaled air from traveling down the air tube 12. Also, as the user inhales, the one-way valve 11a prevents air from the ambient environment from entering through the one-way valve 11a and into the non-porous face mask 11. The exhaled air exits the non-porous face mask 11 through the one-way valve 11a. This exhaled air was not sterilized before exiting the non-porous face mask 11. The germicidal mask system 10 could be used by those who are easily susceptible to colds, the flu, or other contagious diseases. In this case, the only concern of the germicidal system 10 is to prevent the user from being exposed to germs, viruses, and other pathogens in the air of the ambient environment.

The sterilization chamber 13 has a cover 13b with an air passageway 13a formed thereon and leading into the sterilization chamber 13 as discussed above. The sterilization chamber 13 is suspended around the neck of the user by the use of a neck strap 14 attached to the sterilization chamber through the use of loops 13f and 13h. Below the sterilization chamber 13, and attached thereto, is a battery pack 17 similar to the battery pack 7 used in the germicidal mask system 1. Battery pack 17 also contains a dc/ac converter, d.c. rechargeable battery, and power level warning circuit as used in the first embodiment. A warning light 17a lights up when the battery is low. The warning light is initially activated before the battery is too low to operate the miniature ultra-violet lamp. An audible warning signal may be used in conjunction with or in lieu of the warning light 17a.

As shown in FIG. 4, an optional battery pack 16 may be used in conjunction with or lieu of battery pack 17. Battery pack 16 could be connected to the miniature ultra-violet lamp 13c (see FIG. 5) of the sterilization chamber 13 by an electrical wire 15 and can be attached to an article of clothing of the user, such as the belt as illustrated in FIG. 4.

Figure 5:
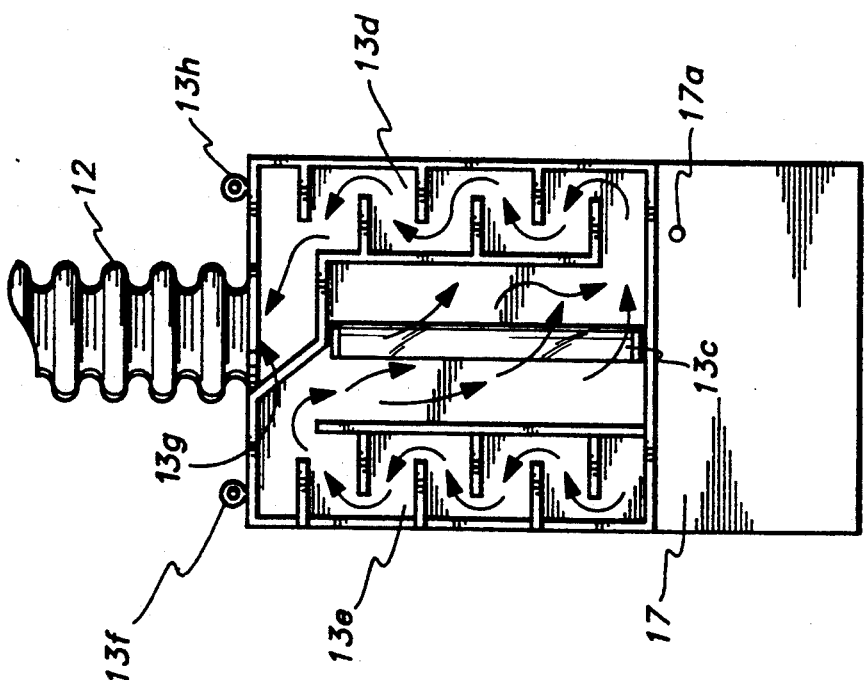
FIG. 5 is a front view of the second embodiment of the present invention with the cover removed.

With the cover 13b of the sterilization chamber 13 removed, the sterilization chamber 13b appears as in FIG. 5. The miniature ultra-violet light source is located therein with a baffle arrangement 13e located on the side of the sterilization chamber in which the air passageway 13a is located when the cover 13a is attached thereto. When the user inhales, air would enter the lower part of the baffle arrangement 13e after entering the air passageway 13a. As in the first embodiment with the germicidal mask system 1, the baffle arrangement 13e prevents the ultraviolet radiation emitted by the miniature ultra-violet lamp 13c from exiting to the ambient environment, while a baffle arrangement 13d prevents ultra-violet radiation from entering the air tube 13 through opening 13g.

Figure 6:
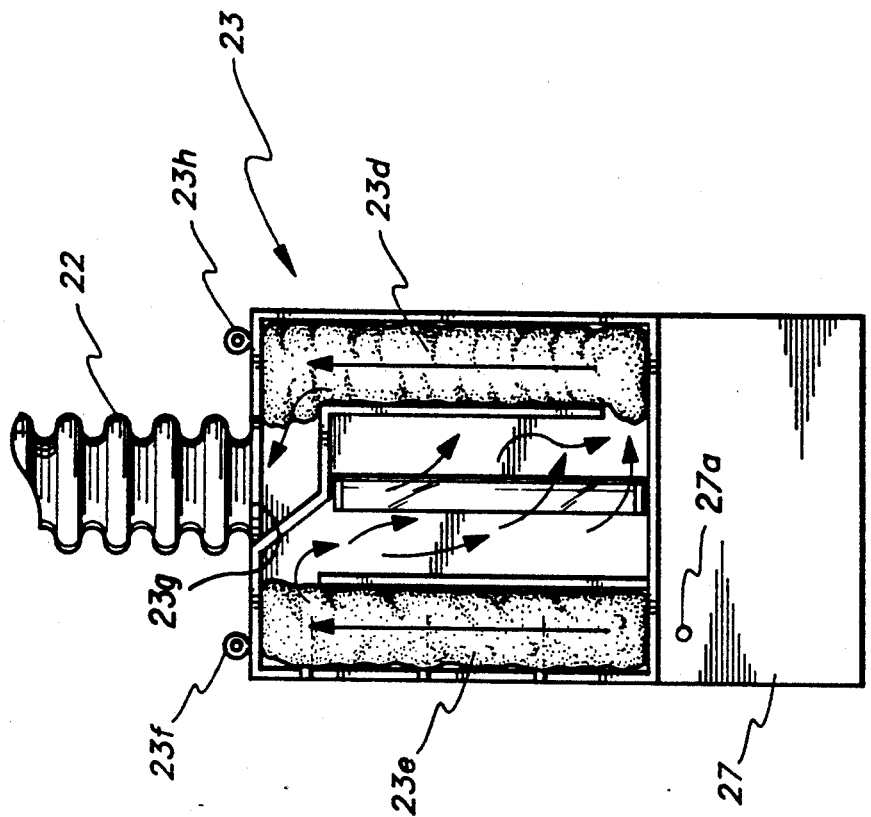
FIG. 6 is a front view of a modified version of the second embodiment of the present invention with the cover removed.

In FIG. 6 is shown an alternative way for preventing the leakage of the ultra-violet radiation from the sterilization chamber. The baffle arrangements 13e and 13d as used in the sterilization chamber 13, see FIG. 5, are replaced with porous materials 23e and 23d in the sterilization chamber 23. Otherwise, sterilization chamber 23 is identical to sterilization chamber 13. Sterilization chamber 23 has loops 23f and 23h which are identical to loops 13f and 13h used in sterilization chamber 13. Further, air tube 22 and opening 23g are identical to air tube 12 and opening 13g as shown in FIG. 5 for sterilization chamber 13.

While various embodiments of the present invention have been presented above, these embodiments are not intended to limit the scope of the invention, which includes all of the embodiments presented in the following claims.

I claim:

1. A germicidal mask, comprising:
a non-porous face mask attachable over the nose and mouth of a user so as to provide an airtight fit thereover;
a sterilization chamber for killing undesirable microorganism contained therein;

a first air passageway allowing air to flow between said non-porous face mask and said sterilization chamber;

a second air passageway allowing air to flow between the ambient environment of the user and said sterilization chamber; and ultra-violet radiation generating means located within said sterilization chamber which emits radiation deadly to said undesirable microorganisms, wherein said sterilization chamber is made from material impervious to said radiation.

2. The germicidal mask according to claim 1, wherein said sterilization chamber further comprises first radiation blocking means preventing any radiation from leaking out from said sterilization chamber into said first air passageway.

3. The germicidal mask according to claim 2, wherein said sterilization chamber comprises second radiation blocking means preventing any radiation from leaking out from said sterilization chamber into said second air passageway.

4. The germicidal mask according to claim 1, wherein both said first radiation blocking means and said second radiation blocking means comprise baffles, said baffles comprising a material impervious to ultra-violet light.

5. The germicidal mask according to claim 1, wherein both said first radiation blocking means and said second radiation blocking means comprise foam, said foam being impervious to ultra-violet light.

6. The germicidal mask according to claim 1, wherein said ultra-violet generating means comprises a miniature ultra-violet radiation lamp.

7. The germicidal mask according to claim 6, further comprising:

a battery pack for supplying power to said ultra-violet lamp, thereby activating said miniature ultra-violet lamp so as to produce said ultra-violet radiation; and an electrical connection having a first end connected to said miniature ultra-violet lamp and a second end connected to said battery pack.

8. The germicidal mask according to claim 6, wherein said battery pack further comprises:

a rechargeable battery for supplying a direct current voltage; and a converter having an input connected to said rechargeable battery and an output connected to said second end, wherein said converter supplies an alternating current voltage at its output.

9. The germicidal mask according to claim 8, further comprising:

means for rigidly and securely attaching said sterilization chamber to said non-porous face mask; and means for selectively attaching and removing said battery pack to an article of clothing of said user.

10. The germicidal mask according to claim 9, further comprising a disposable moisture absorbing cartridge which may be selectively placed into or removed from said sterilization chamber.

11. The germicidal mask according to claim 8, further comprising:

a first one-way valve connected to said non-porous face mask for allowing air to exit therethrough into the ambient environment while preventing air from entering therethrough from said ambient environment;

a second one-way valve connected to said non-porous face mask for allowing air to enter therethrough from said first air passageway while preventing air from exiting therethrough into said first air passageway;

a neck strap;

means for attaching said neck strap to said sterilization chamber for allowing it to be hung around the neck of the user;

power level detecting means for detecting when the power of said rechargeable battery is low;

a battery life indicator for alerting the user when the power of said rechargeable battery is low as indicated by said power level detecting means, thereby informing the user that said rechargeable battery should be recharged.

12. The germicidal mask according to claim 11, said non-porous face mask comprising a clear flexible plastic material, said first air passageway comprising a flexible clear plastic hose leading from said non-porous face mask to said sterilization chamber, and said battery life indicator comprising an indicator lamp located on said sterilization chamber.

13. The germicidal mask according to claim 12, further comprising means for rigidly and securely attaching said battery pack to said sterilization chamber.

14. The germicidal mask according to claim 12, further comprising means for selectively attaching and removing said battery pack to an article of clothing of said user.

15. The germicidal mask according to claim 1, wherein said second radiation blocking means comprises a porous filtering material.

* * * * *